United States Patent
Fukuhara et al.

(10) Patent No.: US 7,988,739 B2
(45) Date of Patent: Aug. 2, 2011

(54) MULTI-COMPONENT HAIR DYE COMPOSITION

(75) Inventors: Masaki Fukuhara, Tokyo (JP); Masayoshi Nojiri, Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 12/682,071

(22) PCT Filed: Oct. 10, 2008

(86) PCT No.: PCT/JP2008/002881
§ 371 (c)(1), (2), (4) Date: Apr. 8, 2010

(87) PCT Pub. No.: WO2009/047913
PCT Pub. Date: Apr. 16, 2009

(65) Prior Publication Data
US 2010/0269268 A1    Oct. 28, 2010

(30) Foreign Application Priority Data
Oct. 12, 2007   (JP) .................. 2007-267056

(51) Int. Cl.
    *A61Q 5/10*    (2006.01)
(52) U.S. Cl. .............. 8/405; 8/431; 8/587; 8/602
(58) Field of Classification Search .......... 8/405, 453, 8/455, 465, 589, 676, 431, 587, 602
    See application file for complete search history.

(56) References Cited

U.S. PATENT DOCUMENTS 4,314,810 A * 2/1982 Fourcadier et al. ............. 8/410

FOREIGN PATENT DOCUMENTS

| JP | 1 275519    | 11/1989 |
| JP | 2000 336020 | 12/2000 |
| JP | 2004 262885 | 9/2004  |
| JP | 2005 179210 | 7/2005  |
| JP | 2006 160641 | 6/2006  |
| JP | 2006 315978 | 11/2006 |

OTHER PUBLICATIONS

STIC Search Report dated Sep. 22, 2010.*
U.S. Appl. No. 12/682,618, filed Apr. 12, 2010, Fukuhara, et al.

* cited by examiner

*Primary Examiner* — Eisa B Elhilo
(74) *Attorney, Agent, or Firm* — Oblon, Spivak, McClelland, Maier & Neustadt, L.L.P.

(57) ABSTRACT

A multi-component hair dye composition excellent in bleaching property and dyeing property including components (a), (b) and (c) which are mixed upon use: (a) one or more kinds of glycylglycine derivative represented by general formula (1) and having two or three amino acid residues, or salts thereof; [wherein X represents a bivalent hydrocarbon group having 1 to 4 carbon atoms which may be substituted with a hydroxyl group, or an amino acid residue; Y represents an amino acid residue, or a bivalent group represented by general formula (2): (wherein symbol -* represents a bond that binds to an adjacent carbonyl group or oxygen atom); R represents a hydrogen atom, or a monovalent hydrocarbon group having 1 to 4 carbon atoms in which the hydroxy group may be substituted; and m and n each represent 0 or 1, provided that when both m and n represent 1, X is not an amino acid residue]; (b) an alkali agent; and c) an oxidizing agent; wherein formula (I) is:

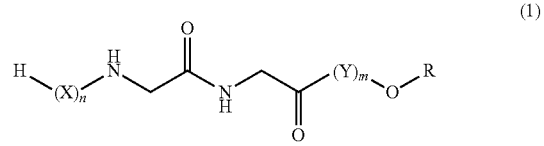

(1)

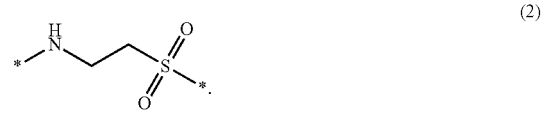

(2)

17 Claims, No Drawings

MULTI-COMPONENT HAIR DYE COMPOSITION

FIELD OF THE INVENTION

The present invention relates to a multi-component hair dye composition and a method for dyeing hair using the same.

BACKGROUND OF THE INVENTION

In hair dyeing process, an oxidative hair dye composed of a first part containing an alkali agent, a precursor and a coupler, and a second part containing hydrogen peroxide, has been generally used.

Preferably, such a hair dye composition has superior dyeing properties, in order to dye the hair in a shorter time and dye the hair more vividly. As a convenient method for enhancing the hair dyeing properties, for example, a method of increasing the concentration of incorporated dye is used. However, if the dye concentration is merely increased, the tinge of color obtained is altered, further an adverse effect may be brought to the stability of formulation. Thus, there have been limitations on the increase in the concentration of dye. Furthermore, a method of increasing the amount of incorporation of the alkali agent or the oxidizing agent and enhancing bleaching properties, to thereby make the change of the dyed-hair color more conspicuous, is also used in combination therewith. However, there have also been limitations in increasing the amount of incorporation of the alkali agent or oxidizing agent because there are problems of, for example, increase of hair damages or the unnatural finish with reduced moist feeling or depth.

In order to solve such problems, methods of using various novel precursors or couplers, or methods of using novel direct dyes have been proposed. However, when these novel dyes are used, enormous efforts are required in adjusting the tinge of color, and therefore, there is a demand for technologies of enhancing dyeing properties using only the conventional dyes which have been widely used, without using novel dyes.

Examples of such technologies that have been proposed include a technology of enhancing dyeing properties by using a hair dye composition containing various cationized protein hydrolysates (Patent Document 1); a technology of enhancing the dyeing properties and bleaching properties at the same time, and thus obtaining higher hair dyeing effects, by using a hair dye composition containing a protein hydrolysate or a derivative thereof, and monoisopropanolamine (Patent Document 2); and the like. In these technologies, use of the hydrolysates of various animal proteins or plant proteins is suggested, however, the composition of the protein hydrolysate varies with the protein source, and moreover, the compositions of different production lots are not always constant. For that reason, the effects described above, provided by the technologies mentioned above, are easy to vary, and are not sufficiently satisfactory.

Patent Document 1: JP-A-H01-275519
Patent Document 2: JP-A-2000-336020

SUMMARY OF THE INVENTION

The present invention provides a multi-component hair dye composition containing components (a), (b) and (c), wherein the components are mixed upon use:

(a) one or more kinds of a glycylglycine derivative represented by general formula (1) and having two or three amino acid residues, or salts thereof;
(b) an alkali agent; and
(c) an oxidizing agent.

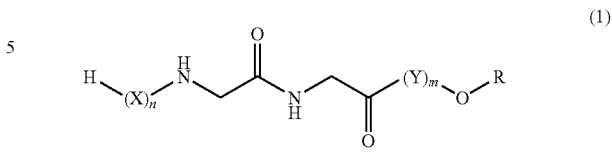

[wherein X represents a bivalent hydrocarbon group having 1 to 4 carbon atoms which may be substituted with a hydroxyl group, or an amino acid residue;

Y represents an amino acid residue, or a bivalent group represented by general formula (2):

(wherein symbol -* represents a bond that binds to an adjacent carbonyl group or oxygen atom);

R represents a hydrogen atom, or a monovalent hydrocarbon group having 1 to 4 carbon atoms in which the hydroxyl group may be substituted; and m and n each represent 0 or 1, provided that when both m and n represent 1, X is not an amino acid residue].

The present invention also provides a method for dyeing hair, including mixing the multi-component hair dye composition immediately before use, applying the hair dye composition to the hair, leaving the hair dye composition on the hair for 1 to 60 minutes, and then rinsing the hair dye composition.

DETAILED DESCRIPTION OF THE INVENTION

The present invention provides a multi-component hair dye composition with excellent bleaching properties and dyeing properties. The present invention also provides a method for dyeing hair with excellent bleaching properties and dyeing properties.

The inventors of the present invention paid attention to various utilizable proteins, and among them, particularly to marine proteins derived from fish scale or fish skin, which are attracting more attention in recent years, and demonstrated the bleaching properties and dyeing properties of a multi-component hair dye composition containing hydrolysates of those proteins. As a result, the inventors have found that it is not necessarily required to use protein hydrolysates for an enhancement of bleaching properties and dyeing properties, rather use of specific oligopeptides may be preferable. Furthermore, according to more detailed investigations of the present invention by the inventors, they have found that a multi-component hair dye composition containing a glycylglycine derivative having a specific structure, an alkali agent and an oxidizing agent provides excellent bleaching properties and dyeing properties at the same time, and the desired hair dyeing effect is provided.

When the multi-component hair dye composition of the present invention is used, high bleaching properties and high dyeing properties can be provided at the same time, and the high dyeing properties are realized even if widely-used conventional dyes are used. Furthermore, according to the present invention, there is provided a method for dyeing hair, which makes it possible to manifest high bleaching properties and high dyeing properties at the same time.

The term "multi-component" in the multi-component hair dye composition of the present invention means that the composition is composed of two or more agents, and examples of the formulation include:

1) a two-component hair dye composition composed of a first part containing the component (b) and a second part containing the component (c), and 2) a three-component hair dye composition composed of a first part containing the component (b), a second part containing the component (c), and a third part containing an oxidizing aid.

The component (a) may be incorporated into any one or more agents among the first part, the second part and the third part mentioned above, or may be incorporated into an independent agent, separately from these agents. Such an independent agent may be in the form of, for example, i) a hair dye pretreating agent of leave on type, which is applied in advance to the hair before a mixed liquid of the first part, the second part, and if necessary, the third part, is applied to the hair, and thereby is mixed with the mixed liquid on the hair;

ii) a hair dye post-treating agent, which is further applied to the hair after a mixed liquid of the first part, the second part and if necessary, the third part, is applied to the hair without rinsing the mixed liquid, and thereby is mixed with the mixed liquid on the hair;

iii) an additive which is additionally mixed in upon preparation of a mixed liquid of the first part, the second part, and if necessary, the third part; and the like. That is, an agent that is mixed with the mixed liquid at the time of application to the hair is included in the class of "independent agent," whereas an agent that is not mixed with the mixed liquid at the time of application to the hair, is not included in the class of "independent agent."

According to the present invention, the case of combining an independent agent with the formulation described above, will also be included in the formulation. That is, a hair dye composition in which an independent agent is further combined with a first part containing the component (b) and a second part containing the component (c), is defined as a two-component hair dye composition, while a hair dye composition in which an independent agent is further combined with a first part containing the component (b), a second part containing the component (c) and a third part containing an oxidizing aid, is defined as a three-component hair dye composition. Furthermore, a hair dye composition in which an independent agent containing the component (a) is combined with a known two-component hair dye composition or a known three-component hair dye composition, is also included in the present invention.

Here, the term "hair dye" as used in the present invention is a concept in which hair bleach without containing dyes, as well as hair coloring agents containing dyes, are included. The term "dye(s), dyeing" means dyeing the hair as well as bleaching the hair in the case of using a hair dye agent containing a dye, and bleaching the hair in the case of using a bleach agent without containing a dye. In addition, the term "whole composition" refers to a composition as a whole that is used in the hair dyeing treatment including up to rinsing, and means a mixture obtained after mixing the respective agents constituting a multi-component hair dye composition, or a combination of such a mixture and an independent agent.

The component (a) is a mixture of one or more kinds of a glycylglycine derivative represented by the general formula (1) or salts thereof, and may be in a free form or may be in the form of amphoteric ion.

Examples of the salts of the glycylglycine derivative include inorganic acid salts such as hydrochloride and sulfate; organic acid salts such as lactate; ammonium salts such as ammonium salts and alkylammonium salts; alkali metal salts such as sodium salts.

In the general formula (1), the bivalent hydrocarbon group having 1 to 4 carbon atoms which may be substituted with a hydroxyl group, as represented by X, may be saturated or unsaturated, and may be a linear or branched chain. Among these, a bivalent saturated hydrocarbon group substituted with a hydroxyl group, or a bivalent saturated hydrocarbon group is preferred.

Examples of the bivalent hydrocarbon group include a methylene group, an ethylene group, an ethylidene group, a vinylene group, a trimethylene group, an isopropylidene group, a 1-propenylene group, a tetramethylene group, a 2-methyltrimethylene group, a 1-methyltrimethylene group, a 1-butenylene group, and the like.

Examples of the bivalent hydrocarbon group substituted with a hydroxyl group include a 1-hydroxyethylene group, a 1-hydroxytrimethylene group, a 1,2-dihydroxytrimethylene group, a 1-hydroxytetramethylene group, a 1,2-dihydroxytetramethylene group, a 1,3-dihydroxytetramethylene group, a 1,2,3-trihydroxytetramethylene group, and the like.

The term "amino acid residue" as used in the present invention means a unit amino acid moiety that is used to form an oligopeptide, which is obtainable by synthesis or is derived from all amino acids that are present in the living body. The "amino acid residue" may be a D-form or an L-form.

In the general formula (1), the amino acid residue represented by X may be an a basic amino acid residue such as an arginine residue, a lysine residue or a histidine residue; an aliphatic amino acid residue such as an alanine residue or a glycine residue; an aromatic amino acid residue such as a phenylalanine residue, a tyrosine residue or a tryptophan residue; an acid amide amino acid residue such as a glutamic residue or an aspartic residue; an acidic amino acid residue such as a glutamic acid residue, an aspartic acid residue or a cysteic acid residue; a hydroxyamino acid residue such as a serine residue or a threonine residue; a cyclic amino acid residue such as a proline residue, an N-methylproline residue or a 4-hydroxyproline residue. Among them, an arginine residue, an alanine residue, a phenylalanine residue, a glycine residue, a glutamine residue, a glutamic acid residue, a serine residue, a proline residue, an N-methylproline residue, and a 4-hydroxyproline residue are preferred.

In the general formula (1), the monovalent hydrocarbon group having 1 to 4 carbon atoms which may be substituted with a hydroxyl group, as represented by R, may be saturated or unsaturated, and may be a linear or branched chain.

The monovalent hydrocarbon group is preferably an alkyl group, and examples include a methyl group, an ethyl group, a propyl group, a butyl group, an isopropyl group, an isobutyl group, an s-butyl group, a t-butyl group, and the like.

The monovalent hydrocarbon group substituted with a hydroxyl group is preferably a hydroxyalkyl group, and examples include a hydroxymethyl group, a 2-hydroxyethyl group, a 3-hydroxypropyl group, a 4-hydroxybutyl group, a 2,3-dihydroxyethyl group, a 2,3,4-trihydroxybutyl group, a 2,4-dihydroxybutyl group, and the like.

In the general formula (1), the amino acid residue represented by Y may be, for example, the same amino acid residues as those represented by X, but Y is preferably an arginine residue, an alanine residue, a glycine residue, a glutamine residue, a glutamic acid residue, a serine residue, a proline residue, a 4-hydroxyproline residue, or a bivalent group represented by general formula (2):

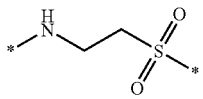
(2)

(wherein symbol -* represents a bond that binds to an adjacent carbonyl group or oxygen atom).

Examples of glycylglycine derivatives that are suitable for the component (a) include the glycylglycine derivatives represented by general formulas (G1) to (G9), and general formulas (G2) to (G9) are more preferred, while general formulas (G8) and (G9) are even more preferred. These glycylglycine derivatives may be in their free forms, may be in the form of amphoteric ion, or may be in the form of salt. These may also be used alone, or in combination of two or more.

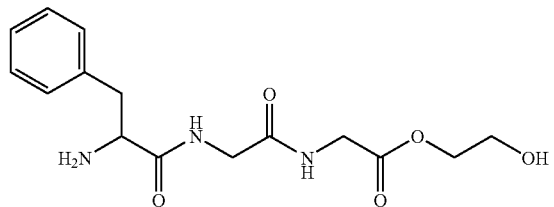
(G1)

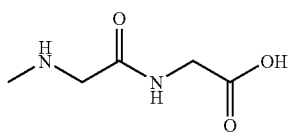
(G2)

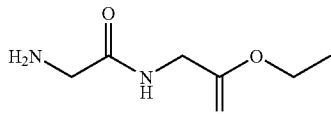
(G3)

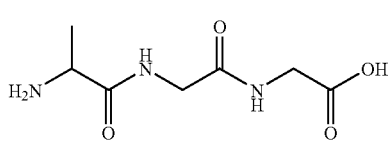
(G4)

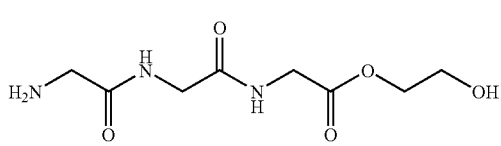
(G5)

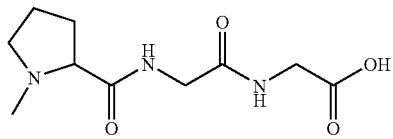
(G6)

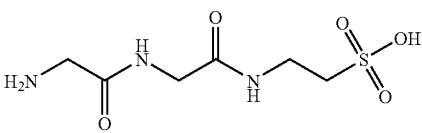
(G7)

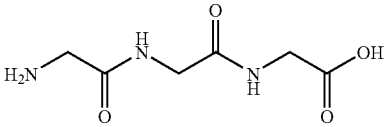
(G8)

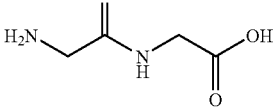
(G9)

The content of the component (a) is preferably 0.05 to 10% by mass, and more preferably 0.25 to 5% by mass, based on the total mass of the composition, from the viewpoints of obtaining the bleaching properties and dyeing properties enhancing effect, and storage stability. Furthermore, the component (a) may be incorporated into any one or more among the first part, the second part and the third part, or may be incorporated into an independent agent.

The alkali agent of the component (b) can be contained in the first part. Examples of the alkali agent include ammonia and salts thereof; alkanolamines such as monoethanolamine, isopropanolamine, 2-amino-2-methylpropanol and 2-aminobutanol, and salts thereof; alkanediamines such as 1,3-propanediamine, and salts thereof; carbonates such as guanidine carbonate, sodium carbonate, potassium carbonate, sodium hydrogen carbonate and potassium hydrogen carbonate; and the like. Among them, ammonia, alkanolamines and salts thereof are preferred.

These alkali agents may be used alone or in combination of two or more. The content of the alkali agent is preferably 0.05 to 10% by mass, more preferably 0.1 to 8% by mass, and even more preferably 0.2 to 5% by mass, based on the total mass of the composition, from the viewpoints of obtaining sufficient dyeing properties and bleaching properties, and reducing hair damages or scalp irritation.

The oxidizing agent of the component (c) can be contained in the second part. As the oxidizing agent, a generator of a hydrogen peroxide or an oxygen such as urea peroxide, hydrogen peroxide, melamine peroxide, sodium perborate, potassium perborate, sodium percarbonate and potassium percarbonate are preferable, and among them, hydrogen peroxide is preferable.

The compounds of the component (c) can be used alone or in combination of two or more. The content of the oxidizing agent of the component (c) is preferably 0.1 to 12% by mass, more preferably 0.5 to 9% by mass, and even more preferably 1 to 6% by mass, in terms of the amount of hydrogen peroxide, from the viewpoints of obtaining sufficient dyeing and bleaching effects, and reducing hair damages or scalp irritation.

The multi-component hair dye composition of the present invention may contain an oxidizing aid as a third part.

For the oxidizing aid, oxidizing agents other than the oxidizing agents mentioned above can be used, and for example, persulfates may be used. Specific examples include ammonium persulfate, potassium persulfate, sodium persulfate, and the like, and these are preferably in the form of powder, such as granules.

The oxidizing aids can be used alone or in combination of two or more. The content of the oxidizing aid is preferably 0.1 to 50% by mass, more preferably 1 to 30% by mass, and even more preferably 3 to 25% by mass, based on the total mass of the composition, from the viewpoint of providing sufficient bleaching effects and reducing hair damages or scalp irritation.

The multi-component hair dye composition of the present invention may contain a direct dye or an oxidation dye intermediate in the first-part agent.

Examples of the direct dye include acid dyes, nitro dyes, disperse dyes, basic dyes, the direct dyes described in JP-A-2003-342139, and the like.

Examples of the acid dyes include Blue No. 1, Violet No. 401, Black No. 401, Orange No. 205, Red No. 227, Red No. 106, Yellow No. 203, Acidic Orange No. 3, and the like.

Examples of the nitro dyes include 2-nitro-para-phenylenediamine, 2-amino-6-chloro-4-nitrophenol, 3-nitro-p-hydroxyethylaminophenol, 4-nitro-ortho-phenylenediamine, 4-amino-3-nitrophenol, 4-hydroxypropylamino-3-nitrophenol, HC Blue No. 2, HC Orange No. 1, HC Red No. 1, HC Yellow No. 2, HC Yellow No. 4, HC Yellow No. 5, HC Red No. 3, N,N-bis(2-hydroxyethyl)-2-nitro-para-phenylenediamine, and the like.

Examples of the disperse dyes include Disperse Violet No. 1, Disperse Blue No. 1, Disperse Black No. 9, and the like.

Examples of the basic dyes include Basic Blue No. 99, Basic Brown No. 16, Basic Brown No. 17, Basic Red No. 76, Basic Red No. 51, Basic Yellow No. 57, Basic Yellow No. 87, Basic Orange No. 31, and the like.

The direct dyes may be used alone or in combination of two or more kinds, or the direct dye may be used in combination with an oxidation dye intermediate. The content of the direct dye is preferably 0.001 to 5% by mass, and more preferably 0.01 to 3% by mass, based on the total mass of the composition.

As the oxidative dye intermediate, known precursors and couplers that are used in conventional hair dyes can be used.

Examples of the precursors include para-phenylenediamine, toluene-2,5-diamine, ortho-chloro-para-phenylenediamine, N-phenyl-para-phenylenediamine, N,N-bis(hydroxyethyl)-para-phenylenediamine, 3-methyl-4-aminophenol, 2-hydroxyethyl-para-phenylenediamine, para-aminophenol, para-methylaminophenol, 4-amino-meta-cresol, ortho-aminophenol, salts thereof, and the like.

Examples of the couplers include resorcin, 2-methylresorcin, 1-naphthol, 1,5-dihydroxynaphthalene, 5-amino-ortho-cresol, meta-phenylenediamine, meta-aminophenol, 2,4-diaminophenoxyethanol, 2,6-diaminopyridine, 2-methyl-5-hydroxyethylaminophenol, 2-amino-3-hydroxypyridine and salts thereof, and the like.

The precursors and couplers may be respectively used alone or in combination of two or more. Their contents are respectively preferably 0.01 to 5% by mass, and more preferably 0.1 to 4% by mass, based on the total mass of the composition.

The multi-component hair dye composition of the present invention may contain a surfactant.

As the surfactant, a cationic surfactant, a nonionic surfactant, an amphoteric surfactant and an anionic surfactant can all be used.

The cationic surfactant is preferably, for example, a mono-long-chain alkyl quaternary ammonium salt. Specific examples include cetrimonium chloride, steartrimonium chloride, behentrimonium chloride, stearalkonium chloride, benzalkonium chloride, and the like, and among these, steartrimonium chloride and behentrimonium chloride are preferred.

Examples of the nonionic surfactant include polyoxyalkylene alkyl ether, polyoxyalkylene alkenyl ether, higher fatty acid sucrose ester, polyglycerin fatty acid ester, higher fatty acid mono- or diethanolamide, polyoxyethylene hardened castor oil, polyoxyethylene sorbitan fatty acid ester, polyoxyethylene sorbite fatty acid ester, alkylsaccharide, alkylamine oxide, alkylamidoamine oxide, and the like. Among these, polyoxyalkylene alkyl ether and polyoxyethylene hardened castor oil are preferred, and polyoxyethylene alkyl (C12-14) ether is more preferred.

Examples of the amphoteric surfactant include imidazoline, carbobetaine, amidobetaine, sulfobetaine, hydroxysulfobetaine, amidosulfobetaine, and the like.

Examples of the anionic surfactant include alkylbenzenesulfonate, alkyl or alkenyl ether sulfate, alkyl or alkenyl sulfate, olefin sulfonate, alkanesulfonate, saturated or unsaturated fatty acid salt, alkyl or alkenyl ether carboxylate, α-sulfone fatty acid salt, N-acylamino acid, phosphoric acid monoester or phosphoric acid diester, sulfosuccinic acid ester, and the like. Examples of alkyl ether sulfate include polyoxyethylene alkyl ether sulfate. Examples of the counterion of the anionic group of these anionic surfactants include alkali metal ions such as sodium ion and potassium ion; alkaline earth metal ions such as calcium ion and magnesium ion; ammonium ion; and alkanolamine having one to three alkanol groups, each having 2 or 3 carbon atoms (for example, monoethanolamine, diethanolamine, triethanolamine, triisopropanolamine, and the like).

The content of the surfactant is preferably 0.1 to 10% by mass, and more preferably 0.5 to 8% by mass, based on the total mass of the composition, from the viewpoint of feel to the touch and the emulsifying performance.

The multi-component hair dye composition of the present invention may contain a cationic polymer.

The cationic polymer refers to a polymer having a cationic group or a group that can be ionized into a cationic group, and also includes amphoteric polymers which are cationic on the whole. That is, the cationic polymer may be a water-soluble polymer containing an amino group or an ammonium group in a side chain of the polymer chain, or a water-soluble polymer containing a diallyl quaternary ammonium salt as a constituent unit. Specific examples include cationized celluloses, cationic starch, cationized guar gum, polymers or copolymers of a diallyl quaternary ammonium salt, quaternized polyvinylpyrrolidone, and the like. Among these, polymers containing a diallyl quaternary ammonium salt as a constituent unit, quaternized polyvinylpyrrolidone and cationized celluloses are preferred from the viewpoint of their effects on softness, smoothness and easy finger-combing during shampooing, and easy manageability and moisture retention during drying, and stability of the agent, and polymers or copolymers of a diallyl quaternary ammonium salt, and cationized celluloses are more preferred.

Specific examples of the cationic polymer include dimethyldiallylammonium chloride polymers (polyquaternium-6, for example, Merquat 100; Nalco Company), dimethyldiallylammonium chloride/acrylic acid copolymers (polyquaternium-22, for example, Merquat 280 and 295; Nalco Company), dimethyldiallylammonium chloride/acrylamide copolymers (polyquaternium-7, for example, Merquat 550; Nalco Company), quaternized polyvinylpyrrolidone (Gafquat 734, Gafquat 755 and Gafquat 755N; ISP Corp.), cationized celluloses (Reogard G and Reogard GP; Lion Cop., Polymer JR-125, Polymer JR-400, Polymer JR-30M, Polymer LR-400, and Polymer LR-30M; all by Union Carbide Corp.), and the like.

These cationic polymers may be used alone, or in combination or two or more. The content of the cationic polymer is preferably 0.001 to 10% by mass, more preferably 0.01 to 8% by mass, and even preferably 0.05 to 5% by mass, based on the total mass of the composition, from the viewpoints of enhancing effect of feel to the touch and formulation stability.

The multi-component hair dye composition of the present invention preferably contains silicone, so as to impart excellent sense of use.

Examples of the silicone include polysiloxanes, modified silicones (for example, amino-modified silicones, fluorine-modified silicones, alcohol-modified silicones, polyether-modified silicones, epoxy-modified silicones, alkyl-modified silicones, and the like), and cyclic polysiloxanes, and among them, polysiloxanes and amino-modified silicones are preferred.

These silicones are commercially available, and for example, BY11-026, BY22-19, FZ-3125, SH200-1,000,000 cs (Dow Corning Toray Co., Ltd..), TSF451-100MA (Momentive Performance Materials Japan LLC) [polysiloxanes]; TSF4440 (Momentive Performance Materials Japan LLC), KF-6005, KF-6011 (Shin-Etsu Chemical Co., Ltd.) [polyether-modified silicones]; SF8451C, SF8452C, SF8457C, SM8704C, SM8904, CF1046 (Toray Dow Corning Silicone Co., Ltd.), KF-867 (Shin-Etsu Chemical Co., Ltd.) [amino-modified silicones]; and the like may be included.

The content of the above silicone is preferably 0.02 to 20% by mass, more preferably 0.1 to 10% by mass, and even more preferably 0.2 to 5% by mass, based on the total mass of the composition, from the viewpoint of providing sufficient effects and suppressing stickiness.

It is preferable for the multi-component hair dye composition of the present invention to contain a higher alcohol, from the viewpoint of improving feel to the touch and stability. The higher alcohol can form a structure with the surfactant, to thereby prevent separation of the hair dye composition as well as to improve feel to the touch during rinsing.

The higher alcohol is preferably an alcohol having 8 to 22 carbon atoms, and even more preferably 16 to 22 carbon atoms. Specific examples include cetanol, stearyl alcohol, behenyl alcohol, and the like, and mixtures thereof may also be used.

The higher alcohols may be used alone or in combination of two or more. The content thereof is preferably 0.01 to 15% by mass, and more preferably 0.1 to 10% by mass, based on the total mass of the composition.

In the multi-component hair dye composition of the present invention, water, and if necessary, an organic solvent can be used as media.

Examples of the organic solvent include lower alkanols such as ethanol and 2-propanol; aromatic alcohols such as benzyl alcohol and benzyloxyethanol; polyols such as propylene glycol, 1,3-butanediol, diethylene glycol and glycerin; cellosolves such as ethylcellosolve and butylcellosolve; and carbitols such as ethylcarbitol and butylcarbitol.

The multi-component hair dye composition of the present invention can contain other components that are conventionally used as cosmetic raw materials, in addition to the components described above. Examples of these components include hydrocarbons, animal and plant oils and fats, higher fatty acids, natural or synthetic macromolecular ethers, antiseptics, chelating agents, stabilizers, antioxidants, plant extracts, crude drug extracts, vitamins, fragrances, and ultraviolet absorbents.

The multi-component hair dye composition of the present invention preferably has a pH at 25° C. of 8 to 12 during use (during mixing), and more preferably a pH 9 to 11, from the viewpoint of dyeing and bleaching effects and skin irritancy.

As a pH adjusting agent, an inorganic acid such as hydrochloric acid or phosphoric acid; an organic acid such as citric acid, glycolic acid or lactic acid; a hydrochloric acid salt such as hydrochloric acid monoethanolamine; a phosphoric acid salt such as monopotassium dihydrogen phosphate or disodium monohydrogen phosphate; or the like can be used, in addition to the alkali agent of the component (b). The pH of the first part before mixing is preferably 8 to 12, and the pH of the second part before mixing is more preferably 2 to 5.

The dosage form of the respective agents constituting the multi-component hair dye composition of the present invention can be in the form of, for example, solution, emulsion, cream, gel, paste, mousse, aerosol, or the like. The dosage form of the third part may be a powder.

The multi-component hair dye composition of the present invention preferably has viscosity enough to prevent liquid dripping when each agent constituting the composition is mixed and applied to the hair. For example, the viscosity of the whole composition measured at 25° C. with a helical stand-equipped type B rotary viscometer (type B8R viscometer, Tokimec, Inc.), is 2000 to 100,000 mPa·s. The viscosity herein is the value obtained after rotating the composition for one minute at 10 rpm using a Rotor T-C.

The multi-component hair dye composition of the present invention is applied to the hair after the respective agents constituting the hair dye composition (including the independent agent previously described) are mixed upon use, and the treatment method using the same includes, for example, applying the composition to the hair, subsequently leaving the composition to stand for a predetermined time, rinsing the composition and drying the hair. The temperature for application to the hair is preferably 15 to 45° C., and the time for application is preferably 1 to 60 minutes. In this case, the multi-component hair dye composition may be lightly rinsed with water, and then the hair may be cleansed using a shampoo containing an anionic surfactant, and subsequently rinsed with water. When the multi-component hair dye composition contains a cationic polymer and a silicone, after the cationic polymer appropriately being washed out, the silicone appropriately remains on the hair, so that satisfactory conditioning effects can be imparted. The shampoo is suitably a common aqueous shampoo containing about 5 to 20% by mass of an anionic surfactant such as sodium lauryl sulfate, sodium laureth-1 sulfate, sodium laureth-2 sulfate or sodium laureth-3 sulfate.

EXAMPLES

Example 1 and Comparative Example 1

A first part, the composition shown in Table 1, and a second part, the composition shown in Table 2, were prepared by conventional methods. A multi-component hair dye composition prepared by combining the obtained first part and second part, not containing any dye, was prepared by mixing the first part and the second part at a mass ratio of 1:1.5, and then the composition was subjected to an evaluation of bleaching properties according to the following evaluation method.

[Evaluation Method of Bleaching Properties]

A mixture of the first part and the second part was applied to a tress of Chinese black hair (manufactured by Beaulax Co., Ltd.) at a bath ratio (part:hair) of 1:1. The mixture was incubated for 25 minutes at 30° C., and then was rinsed with water at about 40° C. The hair tress was washed with a commercially available shampoo, rinsed with water, applied with a commercially available conditioner, and then rinsed with water. The hair tress was towel-dried. The color tone of the hair tress obtained by treating as such was measured with the CIE color specification system (L*, a*, b*) using a colorimeter (Chroma meter CR-400 manufactured by Konica Minolta Sensing, Inc.), and Δb* was calculated by the following formula. Here, the measurement was carried out using three or more samples, and the deviation between the average value and each measured value was ±0.3 or less. The average value was shown in Table 1. A larger value of Δb* means more excellent bleaching properties.

$$\Delta b^* = b^*_2 - b^*_1$$

[wherein $b^*_1$ represents the b* value of before bleaching, and $b^*_2$ represents the b* value of after bleaching].

TABLE 1

First part (unit: mass %)

| Component | Example 1 | Comparative Example 1 |
|---|---|---|
| Glycylglycine derivative (G9) | 2.5 | — |
| Propylene glycol | 4.0 | 4.0 |
| Ascorbic acid | 0.4 | 0.4 |
| Sodium sulfite | 0.4 | 0.4 |
| EDTA-4Na | 0.1 | 0.1 |
| Steartrimonium chloride | 1.4 | 1.4 |
| Ceteth-40 | 2.5 | 2.5 |
| Cetearyl alcohol | 8.0 | 8.0 |
| Dimethicone*[1] | 2.0 | 2.0 |
| Amodimethicone*[2] | 1.0 | 1.0 |
| Aqueous ammonia (28 mass %) | 7.0 | 7.0 |
| Fragrance | 0.5 | 0.5 |
| Ethanolamine*[3] | q.s. | q.s. |
| Water | Balance | Balance |
| Total | 100 | 100 |
| pH after mixing of first part and second part (25° C.) | 9.6 | 9.8 |
| Average value of bleaching properties (Δb*) | 5.9 | 5.0 |

*[1]CF1046, Toray Dow Corning Silicone Co., Ltd.
*[2]SM8704C, Toray Dow Corning Silicone Co., Ltd.
*[3]Amount to adjust the pH to 10.7

TABLE 2

Second part

| Component | (mass %) |
|---|---|
| Cetanol | 2.0 |
| Sodium Lauryl sulfate | 1.0 |
| Aqueous hydrogen peroxide (35 mass %) | 17.0 |
| Methylparaben | 0.1 |
| Phosphoric acid*[4] | q.s. |
| Water | Balance |
| Total | 100 |

*[4]Amount to adjust the pH to 3.5

As shown in Table 1, the bleach composition of Example 1 had excellent bleaching properties as compared with Comparative Example 1.

Examples 2 and 3, and Comparative Examples 2 and 3

A first part, the composition shown in Table 3, and a second part, the composition shown in Table 2, were prepared according to conventional methods. A multi-component hair dye composition prepared by combining the obtained first part and second part was prepared by mixing the first part and the second part at a mass ratio of 1:1.5, and then the composition was subjected to an evaluation of dyeing properties according to the following evaluation method.

[Dyeing Properties Evaluation Method]

A mixture of the first part and the second part was applied to a tress of Chinese white hair (manufactured by Beaulax Co., Ltd.) at a bath ratio (part:hair) of 1:1. The mixture was incubated for 25 minutes at 30° C., and then was rinsed with water at about 40° C. The hair tress was washed with a commercially available shampoo, rinsed with water, applied with a commercially available conditioner, and then rinsed with water. The hair tress was towel-dried. The color tone of the hair tress obtained by treating as such was measured with the CIE color specification system (L*, a*, b*) using a colorimeter (Chroma meter CR-400 manufactured by Konica Minolta Sensing, Inc.), and ΔE* was calculated by the following expression. Here, the measurement was carried out with three or more samples, and the deviation between the average value and each measured value was ±1.2 or less. The average value is shown in Table 3. A larger value of ΔE* means more excellent dyeing properties.

$$\Delta E^* = \sqrt{(L^*_2 - L^*_1)^2 + (a^*_2 - a^*_1)^2 + (b^*_2 - b^*_1)^2}$$

[wherein $L^*_1$, $a^*_1$ and $b^*_1$ represent the values of L*, a* and b* of before dyeing, respectively, and $L^*_2$, $a^*_2$ and $b^*_2$ represent the values of L*, a* and b* of after dyeing, respectively].

TABLE 3

First part (unit: mass %)

| | Example | | Comparative Example | |
|---|---|---|---|---|
| Component | 2 | 3 | 2 | 3 |
| Glycylglycine derivative (G9) | 5.0 | — | — | — |
| Glycylglycine derivative (G8) | — | 5.0 | — | — |
| Marine protein hydrolysate (20 mass % aqueous solution) *[5] | — | — | — | 25.0 |
| Para-aminophenol | 0.3 | 0.3 | 0.3 | 0.3 |
| Resorcin | 0.3 | 0.3 | 0.3 | 0.3 |
| Toluene-2,5-diamine | 0.6 | 0.6 | 0.6 | 0.6 |
| 5-Amino-ortho-cresol | 0.1 | 0.1 | 0.1 | 0.1 |
| Propylene glycol | 4.0 | 4.0 | 4.0 | 4.0 |
| Ascorbic acid | 0.4 | 0.4 | 0.4 | 0.4 |
| Sodium sulfite | 0.4 | 0.4 | 0.4 | 0.4 |
| EDTA-4Na | 0.1 | 0.1 | 0.1 | 0.1 |
| Steartrimonium chloride | 1.4 | 1.4 | 1.4 | 1.4 |
| Ceteth-40 | 2.5 | 2.5 | 2.5 | 2.5 |
| Cetearyl alcohol | 8.0 | 8.0 | 8.0 | 8.0 |
| Dimethicone *[6] | 2.0 | 2.0 | 2.0 | 2.0 |
| Amodimethicone *[7] | 1.0 | 1.0 | 1.0 | 1.0 |
| Aqueous ammonia (28 mass %) | 6.5 | 6.5 | 6.5 | 6.5 |
| Fragrance | 0.5 | 0.5 | 0.5 | 0.5 |
| Ethanolamine *[8] | q.s. | q.s. | q.s. | q.s. |

TABLE 3-continued

First part (unit: mass %)

| Component | Example 2 | Example 3 | Comparative Example 2 | Comparative Example 3 |
|---|---|---|---|---|
| Water | Balance | Balance | Balance | Balance |
| Total | 100 | 100 | 100 | 100 |
| pH after mixing of first part and second part (25° C.) | 9.7 | 9.7 | 9.8 | 9.8 |
| Average value of dyeing properties (ΔE*) | 37.0 | 37.5 | 32.2 | 32.9 |

*5: W-42M, Seiwa Kasei Co., Ltd.
*6: CF1046, Toray Dow Corning Silicone Co., Ltd.
*7: SM8704C, Toray Dow Corning Silicone Co., Ltd.
*8: Amount to adjust the pH to 10.7

As shown in Table 3, the multi-component hair dye compositions of Examples 2 and 3 both had excellent dyeing properties as compared with the compositions of Comparative Examples 2 and 3.

Example 4

A multi-component hair dye composition prepared by preparing a first part, the composition shown in Table 4, according to a conventional method, and combining the first part with a second part, the composition shown in Table 2, was prepared by mixing the first part and the second part at a mass ratio of 1:2 (pH (25° C.) 9.6), and the dyeing properties were evaluated in the same manner as in Examples 2 and 3. The results are shown together in Table 4.

TABLE 4

First part (unit: mass %)

| Component | Example 4 |
|---|---|
| Glycylglycine derivative (G9) | 2.5 |
| Para-aminophenol | 0.6 |
| Toluene-2,5-diamine | 0.5 |
| Meta-aminophenol | 0.18 |
| Resorcin | 0.7 |
| 5-Amino-ortho-cresol | 0.1 |
| Propylene glycol | 4.0 |
| Ascorbic acid | 0.4 |
| Sodium sulfite | 0.4 |
| EDTA-4Na | 0.1 |
| Sodium lauryl sulfate | 1.0 |
| Ceteth 40 | 2.5 |
| Cetearyl alcohol | 8.0 |
| Dimethicone*9 | 2.0 |
| Amodimethicone*10 | 1.0 |
| Ethanolamine | 1.5 |
| Aqueous ammonia (28 mass %) | 6.5 |
| Fragrance | 0.5 |
| Ammonium hydrogen carbonate*11 | q.s. |
| Water | Balance |
| Total | 100 |
| Average value of dyeing properties (ΔE*) | 42.3 |

*9CF1046, Toray Dow Corning Silicone Co., Ltd.
*10SM8704C, Toray Dow Corning Silicone Co., Ltd.
*11Amount to adjust the pH to 10

The multi-component hair dye composition of Example 4 had excellent dyeing properties.

Formulation Examples 1 to 3

A first part, the composition shown in Table 5, and a second part, the composition shown in Table 2, were mixed at a mass ratio of 1:1, and the mixture was applied to the hair at a bath ratio (part:hair) of 1:1, and was incubated for 30 minutes at room temperature. Subsequently, the mixture was rinsed with water, washed with a commercially available shampoo, and then dried.

TABLE 5

First part (unit: mass %)

| Component | Formulation Example 1 | Formulation Example 2 | Formulation Example 3 |
|---|---|---|---|
| Glycylglycine derivative (G5) | 0.25 | — | 0.25 |
| Glycylglycine derivative (G6) | — | 0.25 | 0.25 |
| Para-aminophenol | 0.1 | 0.1 | — |
| Toluene-2,5-diamine sulfate | 0.1 | — | 0.2 |
| 5-Amino-ortho-cresol | — | — | 0.2 |
| Meta-aminophenol | 0.2 | 0.1 | — |
| Basic Blue No. 99 | — | — | 0.2 |
| Basic Brown No. 16 | — | 0.1 | — |
| HC Yellow No. 4 | 0.05 | — | — |
| HC Yellow No. 2 | — | 0.05 | — |
| Behentrimonium chloride | 2.1 | 2.1 | 2.1 |
| Liquid paraffin | 0.5 | 0.5 | 0.5 |
| Propylene glycol | 7.0 | 7.0 | 7.0 |
| Cetearyl alcohol | 7.0 | 7.0 | 7.0 |
| Polyquaternium-10*12 | 1.0 | 1.0 | 1.0 |
| Amodimethicone*13 | 1.5 | 1.5 | 1.5 |
| Ammonia (28 mass %) | 6.5 | 6.5 | 6.5 |
| Ammonium chloride*14 | q.s. | q.s. | q.s. |
| Purified water | Balance | Balance | Balance |
| Total | 100 | 100 | 100 |
| pH after mixing of first part and second part (25° C.) | 9.7 | 9.7 | 9.7 |

*12Ucare Polymer JR-400, Amerchol Corp.
*13SM8704C, Toray Dow Corning Silicone Co., Ltd.
*14Amount to adjust the pH to 10

Formulation Examples 4 to 6

A first part, the composition shown in the Formulation Examples 1 to 3 of Table 5, a second part, the composition shown in Table 2, and a third part, the composition shown in Table 6, were mixed at a mass ratio of 1:2:0.3 (pH (25° C.) Formulation Example 4: 9.6, Formulation Example 5: 9.6, Formulation Example 6: 9.6), and the mixture was applied to the hair at a bath ratio (part:hair) of 1:1, and was incubated for 30 minutes at room temperature. Subsequently, the mixture was rinsed with water, washed with a commercially available shampoo, and dried (the Formulation examples corresponding to Formulation Examples 1 to 3 were designated as Formulation Examples 4 to 6, respectively).

TABLE 6

Third part

| Component | Mass % |
|---|---|
| Sodium persulfate | 10.0 |
| Pottasium persulfate | 16.0 |
| Ammonium persulfate | 26.0 |
| Sodium metasilicate | 20.0 |
| Sodium silicate | 17.8 |
| Silica | 1.0 |
| Sodium stearate | 5.0 |

TABLE 6-continued

| Third part | |
|---|---|
| Component | Mass % |
| Sodium lauryl sulfate | 1.0 |
| EDTA-4Na | 1.0 |
| Cyclodextrin | 0.2 |
| Xanthan gum | 1.0 |
| Cellulose gum | 1.0 |
| Total | 100 |

Formulation Examples 7 and 8

A first part, the composition shown in Example 2 or Comparative Example 2 of Table 3, a second part, the composition shown in Table 2, and a glycylglycine derivative-containing solution, the composition shown in Table 7, were mixed at a mass ratio of 1:1:0.1 (pH (25° C.) Formulation Example 7: 9.6, Formulation Example 8: 9.7), and the mixture was applied to the hair at a bath ratio (part:hair) of 1:1, and was incubated for 30 minutes at room temperature. Subsequently, the mixture was rinsed with water, washed with a commercially available shampoo, and then dried (the formulation example corresponding to Example 2 was designated as Formulation Example 7, and the formulation example corresponding to Comparative Example 2 was designated as Formulation Example 8).

TABLE 7

| Glycylglycine derivative-containing solution | |
|---|---|
| Component | Mass % |
| Glycylglycine derivative (G9) | 10 |
| Methylparaben | 0.1 |
| Phosphoric acid*[14] | q.s. |
| Water | Balance |
| Total | 100 |

*[14]Amount to adjust the pH to 5.

The invention claimed is:

1. A multi-component hair dye composition comprising as separated components (a), (b) and (c), wherein:
   (a) represents one or more kinds of glycylglycine derivative represented by general formula (1) and having two or three amino acid residues, or salts thereof;

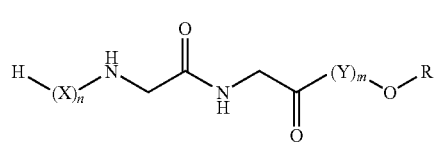

wherein
   X represents a bivalent hydrocarbon group having 1 to 4 carbon atoms which may be substituted with a hydroxyl group, or an amino acid residue;
   Y represents an amino acid residue, or a bivalent group represented by general formula (2):

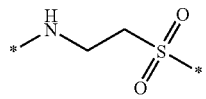

wherein symbol -* represents a bond that binds to an adjacent carbonyl group or oxygen atom;
   R represents a hydrogen atom, or a monovalent hydrocarbon group having 1 to 4 carbon atoms in which the hydroxy group may be substituted; and
   m and n each represent 0 or 1, provided that when both m and n represent 1, X is not an amino acid residue;
   (b) represents at least one alkali agent; and
   (c) represents at least one oxidizing agent;
wherein components (a), (b) and (c), when mixed, produce a composition that has a pH ranging from 9 to 11.

2. A multi-component hair dye composition, comprising as separated components (a), (b) and (c):
   (a) one or more kinds of glycylglycine derivative represented by general formula (1) and having two or three amino acid residues, or salts thereof;

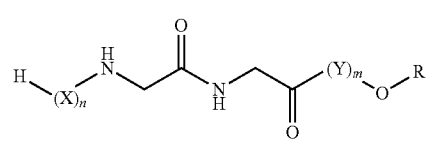

wherein
   X represents a bivalent hydrocarbon group having 1 to 4 carbon atoms which may be substituted with a hydroxyl group, or an amino acid residue;
   Y represents an amino acid residue, or a bivalent group represented by general formula (2):

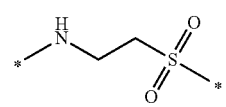

wherein symbol -* represents a bond that binds to an adjacent carbonyl group or an oxygen atom;
   R represents a hydrogen atom, or a monovalent hydrocarbon group having 1 to 4 carbon atoms in which the hydroxy group may be substituted; and
   wherein m and n each represent 0 or 1, at least one of m or n is 1, and when both m and n represent 1, then X is not an amino acid residue;
   (b) an alkali agent; and
   (c) an oxidizing agent;
wherein in the general formula (1) of component (a),
   X represents an arginine residue, an alanine residue, a phenylalanine residue, a glycine residue, a glutamine residue, a glutamic acid residue, a serine residue, a proline residue, an N-methylproline residue, a 4-hydroxyproline residue or a bivalent saturated hydrocarbon group having 1 to 4 carbon atoms;
   Y represents an arginine residue, an alanine residue, a glycine residue, a glutamine residue, a glutamic acid residue, a serine residue, a proline residue, a 4-hydroxyproline residue or a bivalent group represented by the general formula (2); or R represents a hydrogen atom or an alkyl group which may be substituted by a hydroxyl group.

3. The multi-component hair dye composition according to claim 1, wherein the glycylglycine derivative of the component (a) is glycylglycine.

4. The multi-component hair dye composition according to claim 1, wherein the glycylglycine derivative of the component (a) is glycylglycylglycine.

5. The multi-component hair dye composition according to claim 1, having a first part comprising the component (b) and a second part comprising the component (c).

6. A method for dyeing hair, comprising
mixing the multi-component hair dye composition according to claim 1 immediately before use,
applying the hair dye composition to the hair,
leaving the hair dye composition on the hair for 1 to 60 minutes, and then
rinsing the hair dye composition out of the hair.

7. The multi-component hair dye composition of claim 1, wherein (a) represents one or more kinds of glycylglycine derivative represented by general formula (1), wherein n=1 and X is a bivalent hydrocarbon group having 1 to 4 carbon atoms which may be substituted with a hydroxyl group.

8. The multi-component hair dye composition of claim 1, wherein n=1 and (a) represents one or more kinds of glycylglycine derivative represented by general formula (1), wherein X is an amino acid residue.

9. The multi-component hair dye composition of claim 1, wherein n=1 and (a) represents one or more kinds of glycylglycine derivative represented by general formula (1), wherein m=1 and Y represents an amino acid residue, or a bivalent group represented by general formula (2):

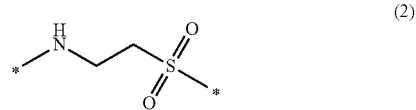

(2)

wherein symbol -* represents a bond that binds to an adjacent carbonyl group or oxygen atom.

10. The multi-component hair dye composition of claim 1, wherein R represents a hydrogen atom.

11. The multi-component hair dye composition of claim 1, wherein R represents a monovalent hydrocarbon group having 1 to 4 carbon atoms in which the hydroxy group may be substituted.

12. The multi-component hair dye composition of claim 1, wherein in general formula (I) of component (a), m is 0 and n is 0.

13. The multi-component hair dye composition of claim 1, wherein in general formula (I) of component (a), m is 1 and n is 0.

14. The multi-component hair dye composition of claim 1, wherein in general formula (I) of component (a), m is 0 and n is 1.

15. The multi-component hair dye composition of claim 1, wherein in general formula (I) of component (a), m is 1 and n is 1.

16. A hair dye composition having a pH ranging from 9 to 11 produced by mixing components (a), (b) and (c) of claim 1.

17. A hair dye composition having a pH ranging from 9 to 11 produced by mixing components (a), (b) and (c) of claim 2.

* * * * *